(12) United States Patent
O'Hara

(10) Patent No.: US 8,074,834 B2
(45) Date of Patent: Dec. 13, 2011

(54) MEDICAL BANDAGING PRODUCT

(75) Inventor: Martin O'Hara, Charlotte, NC (US)

(73) Assignee: BSN Medical, Inc., Charlotte, NC (US)

( * ) Notice: Subject to any disclaimer, the term of this patent is extended or adjusted under 35 U.S.C. 154(b) by 414 days.

(21) Appl. No.: 12/349,812

(22) Filed: Jan. 7, 2009

(65) Prior Publication Data

US 2009/0114664 A1 May 7, 2009

Related U.S. Application Data

(62) Division of application No. 11/867,415, filed on Oct. 4, 2007, now Pat. No. 7,748,531.

(51) Int. Cl.
*B65H 5/28* (2006.01)
*G07F 11/68* (2006.01)

(52) U.S. Cl. ........ 221/1; 206/389; 206/409; 229/125.21

(58) Field of Classification Search .................. 206/440, 206/494, 410, 411, 395, 408, 1.5; 221/303–310; 24/458, 339, 531; 229/76, 77, 78.1, 78.2, 229/79, 80, 82, 84, 125, 125.01–125.42; 225/39, 30
See application file for complete search history.

(56) References Cited

U.S. PATENT DOCUMENTS

| | | |
|---|---|---|
| 1,376,636 A | 5/1921 | Pike |
| 1,973,237 A | 9/1934 | Vilas |
| 2,007,740 A | 7/1935 | Brelsford |
| 2,300,161 A | 10/1942 | Mather |
| 2,342,564 A | 2/1944 | Van Saun |
| 2,373,092 A | 4/1945 | Avery |
| 2,537,801 A | 1/1951 | Swatsick |
| 2,553,840 A | 5/1951 | Andre |
| 2,646,877 A | 7/1953 | Scholl |
| 2,741,419 A | 4/1956 | Janz |
| 3,885,724 A | 5/1975 | Ehrlund |
| 3,900,024 A | 8/1975 | Lauber et al. |

(Continued)

FOREIGN PATENT DOCUMENTS

WO 2006000251 A1 1/2006

(Continued)

OTHER PUBLICATIONS

Office Action dated Jan. 9, 2009, listing cited references, entered in priority U.S. Appl. No. 11/867,415.

(Continued)

*Primary Examiner* — J. Gregory Pickett
*Assistant Examiner* — Andrew Perreault
(74) *Attorney, Agent, or Firm* — Shumaker, Loop & Kendrick, LLP

(57) ABSTRACT

A method of dispensing and resealing a moisture curable medical material against moisture intrusion is provided. The method includes the steps of providing a moisture-impervious product container comprising an elongate sleeve sealable to prevent entry of moisture, providing an elongate medical material positioned in the sleeve, sealing the medical material in the sleeve against entry of moisture until use, providing a dispensing carton within which the sleeve and medical material positioned therein is contained, and bearing a tab against the length of the sleeve devoid of medical material and into a laterally-extending opening in the sealing member to form a doubled thickness of the sleeve having a sealing fold therein to form a seal that is resistant to moisture intrusion into the sleeve.

7 Claims, 11 Drawing Sheets

U.S. PATENT DOCUMENTS

| | | |
|---|---|---|
| 3,923,049 A | 12/1975 | Lauber et al. |
| 4,235,228 A | 11/1980 | Gaylord et al. |
| 4,245,774 A | 1/1981 | Heinz, Jr. |
| 4,382,510 A | 5/1983 | Gaffney |
| 4,632,299 A | 12/1986 | Holmberg |
| 4,673,084 A | 6/1987 | Hubbard et al. |
| 4,676,861 A | 6/1987 | Bishop |
| 4,770,299 A | 9/1988 | Parker |
| 4,772,355 A | 9/1988 | Leahy |
| 4,824,517 A | 4/1989 | Leahy |
| 4,869,046 A | 9/1989 | Parker |
| 4,899,738 A | 2/1990 | Parker |
| 5,003,097 A | 3/1991 | Beaucage et al. |
| 5,003,970 A | 4/1991 | Parker et al. |
| 5,533,621 A | 7/1996 | Schoal, Jr. |
| 5,655,270 A | 8/1997 | Boisvert |
| 5,755,678 A | 5/1998 | Parker et al. |
| 6,719,710 B2 | 4/2004 | Darcey |
| 6,749,551 B2 | 6/2004 | Metzler et al. |
| 6,981,590 B1 | 1/2006 | Ubel et al. |
| 7,694,816 B2 * | 4/2010 | Kilbey et al. ............ 206/440 |
| 2004/0206638 A1 | 10/2004 | Metzler et al. |

FOREIGN PATENT DOCUMENTS

WO    WO2006/000251 A1    1/2006

OTHER PUBLICATIONS

Office Action dated Jul. 24, 2009, listing cited reference, entered in priority U.S. Appl. No. 11/867,415.

* cited by examiner

MEDICAL BANDAGING PRODUCT

CROSS-REFERENCE TO RELATED APPLICATIONS

This application is a divisional of U.S. patent application Ser. No. 11/867,415, filed on Oct. 4, 2007.

TECHNICAL FIELD AND BACKGROUND OF THE INVENTION

The present invention relates generally to the field of orthopedic medicine and more specifically to an improved roll form medical bandage and a container for storing, dispensing and sealing such a roll form bandaging product against moisture intrusion.

Medical bandages for use in the treatment of injuries, such as broken bones requiring immobilization of a body member, are generally formed from a strip of fabric or scrim material impregnated with a substance which hardens into a rigid structure after the strip has been wrapped around the body member. The hardening substance traditionally used in carrying out this procedure is plaster-of-paris.

Conventional practice has been to fabricate a cast or splint upon an injured limb by initially applying to the limb a protective covering of a cotton fabric or the like and then overwrapping the covering and limb with a woven cloth impregnated with plaster-of-paris which has been wetted by dipping in water immediately prior to application. This practice is still in widespread use but possesses several significant disadvantages. For example, the above-described application procedure is messy and time consuming. Several components are required and considerable skill is necessary.

In order to alleviate the above-recited disadvantages of the conventional application procedure for plaster-of-paris casts and splints, unitary splinting materials have been devised and are disclosed in, for example, U.S. Pat. Nos. 3,900,024, 3,923,049, and 4,235,228. All of these patents describe a padding material with a plurality of layers of plaster-of-paris impregnated cloth. Such unitary splinting materials are not as messy and can be applied more quickly but still suffer from a number of disadvantages inherent in plaster-of-paris cast materials. All plaster-of-paris splints have a relatively low strength to weight ratio which results in a finished splint which is very heavy and bulky. Plaster-of-paris splints are slow to harden, requiring 24 to 72 hours to reach maximum strength. Since plaster-of-paris breaks down in water, bathing and showering are difficult. Even if wetting due to these causes can be avoided, perspiration over an extended period of time can break down the plaster-of-paris and create a significant problem with odor and itching.

A significant advance in the art of casting and splinting is disclosed in U.S. Pat. Nos. 4,770,299; 4,869,046; 4899,738 and 5,003,097. The medical material disclosed in these patents is a flexible fabric impregnated with a moisture-curing resin enclosed in a moisture-free, moisture-impervious package, such as an elongate plastic/foil laminated sleeve or bag. Compared to plaster-of-paris, these products are extremely lightweight, have a very high strength-to-weight ratio, and can be made relatively porous, permitting a flow of air through the casting material.

The U.S. Pat. Nos. 4,770,299; 4,869,046; 4899,738 and 5,003,097 also disclose various ways of resealing the package against entry of moisture after a desired length of bandaging material has been removed for use. For example, the '299 patent discloses use of a tape, a spring-loaded compression gasket, a spring-loaded roller or re-heat sealing the envelope to resealing the package between uses. See, '299 patent, col. 4, II. 8-24. The '970 patent discloses use of a spring-loaded clamp or a sandwich bag-type zip lock to reseal the package between uses. See, '970 patent, col. 6, II. 29-41 and FIGS. 11 and 12.

Numerous subsequently-issued patents to present applicant also disclose use of a scissor-type clip as a re-sealing device. See, e.g., U.S. Pat. No. 6,719,710, FIG. 10.

The present invention provides a resealing means that is associated with the carton in which the bandage material is stored.

SUMMARY OF THE INVENTION

It is therefore an object of the invention to provide a medical bandaging product in roll form with a moisture-curable resin which hardens the material upon exposure to moisture to form a rigid, self-supporting structure, that can be dispensed in any desired length while preventing hardening of the remaining material until use is desired by means of a resealing means associated with the carton in which the medical material is packaged for shipment and storage and between uses.

It is another object of the invention to provide a medical bandaging product in roll form that incorporates a clip that cooperates with the carton in which the medical material is packaged for shipment and storage and between uses to effectuate a seal against moisture intrusion between uses.

It is another object of the invention to provide a medical bandaging product in roll form that incorporates a clip that cooperates with the carton in which the medical material is packaged for shipment and storage and between uses to effectuate a seal against moisture intrusion between uses, and that can be removed from the carton for installation and use on another carton, if desired.

These and other objects and advantages are achieved by providing a medical bandaging product, comprising a container formed of moisture-impervious material, a medical material positioned in the container in substantially moisture-free conditions and sealed therein against entry of moisture, and a dispensing carton within which the container and medical material positioned therein is contained. The dispensing carton includes an opening in the carton through which the medical material is removed through an opening in the container, a sealing member carried by the carton adjacent the opening for receiving across the opening in the carton a length of the container devoid of medical material therein, and a tab for bearing against the length of the container devoid of medical material to form a doubled thickness of the container having a sealing fold therein to form a seal that is resistant to moisture intrusion into the container.

According to one preferred embodiment of the invention, the sealing member comprises a generally S-shaped body defining a first slot for receiving the tab and doubled thickness of the container, and a second slot for retaining the sealing member on the carton adjacent the opening.

According to another embodiment of the invention, the tab is formed on the end of a carton flap that is movable between an open position allowing access through the opening to the container in the carton and a closed position wherein the opening in the carton is covered and the container is maintained in sealing position in the first slot by the tab on the end of the carton flap.

According to yet another embodiment of the invention, the container comprises a moisture-impervious sleeve.

According to yet another embodiment of the invention, the S-shaped body includes first gripping members positioned in the first slot for gripping the sleeve, and second gripping members positioned in the second slot for gripping the carton.

According to yet another embodiment of the invention, the second slot has an enlarged mouth for guiding the tab therein.

According to yet another embodiment of the invention, the medical bandaging product comprises an outer sleeve formed of moisture-impervious material, and a medical material positioned in the sleeve in substantially moisture-free conditions and sealed therein against entry of moisture until use. The medical material comprises a substrate having first and second opposing sides defining therebetween a predetermined thickness, a reactive system impregnated into or coated onto the substrate, the system remaining stable when maintained in substantially moisture-free conditions and hardening upon exposure to sufficient moisture to form a rigid, self supporting structure, and a soft, flexible, protective, freely water and air permeable padding overlying both the first and second sides of the substrate contiguous thereto to provide a cushioning barrier between the substrate and the skin of a patient when the material is in use.

According to yet another embodiment of the invention, the length of medical bandaging product is in the form of a coil.

According to yet another embodiment of the invention, the length of medical material is positioned within an elongate sleeve to form a coextensive continuum of medical material and sleeve, and wherein the sleeve with the medical material therein is rolled into a coil.

According to yet another embodiment of the invention, the container comprises an elongate tubular member, and the medical material has substantially the same predetermined length as the elongate tubular member and is positioned in a single coextensive layer in the elongate tubular member.

According to yet another embodiment of the invention, the container comprises a bag having a resealable dispensing opening therein, and the medical material is positioned in roll form within the bag for being dispensed in medically appropriate lengths through the dispensing opening.

According to yet another embodiment of the invention, a medical bandaging product is provided that comprises a flexible container formed of moisture-impervious material, a medical material positioned in the container in substantially moisture-free conditions and sealed therein against entry of moisture, and a dispensing carton within which the container and medical material positioned therein is contained. The dispensing carton includes an opening in the carton through which the medical material is removed through an opening in the container, a generally S-shaped sealing member carried by the carton adjacent the opening for receiving across the opening in the carton a length of the container devoid of medical material therein; and a flap integrally-formed with the carton for pivoting movement between a closed position closing the opening in the carton and an open position allowing removal of the medical material, the flap including a substantially right-angle tab formed on a free end thereof or bearing against and forcing the length of the container devoid of medical material and into the S-shaped sealing member to form a doubled thickness of the flexible container having a sealing fold therein to form a seal that is resistant to moisture intrusion into the container.

According to a method embodiment of the invention, a method of dispensing and resealing a moisture curable medical material against moisture intrusion is provided, comprising the steps of providing a moisture-impervious product container comprising an elongate sleeve sealable to prevent entry of moisture, providing an elongate medical material positioned in the sleeve, and sealing the medical material in the sleeve against entry of moisture until use. The medical material comprises a substrate, a reactive system impregnated into or coated onto the substrate, the system remaining stable when maintained in substantially moisture-free conditions and hardening upon exposure to sufficient moisture to form a rigid, self supporting structure, and a soft, flexible protective wrapping enclosing the substrate along its length to provide a cushioning barrier between the substrate and the skin of a patient when the material is in use. A dispensing carton is provided within which the sleeve and medical material positioned therein is contained. The dispensing carton includes an opening in the carton through which the medical material is removed through an opening in the container, and a sealing member having a laterally-extending opening therein and being carried by the carton adjacent the opening for receiving across the opening in the carton a length of the container devoid of medical material therein. A tab is provided for bearing against the length of the container devoid of medical material to form a doubled thickness of the container having a sealing fold therein, and a medically appropriate length of medical material is dispensed.

The tab is urged against the length of the sleeve devoid of medical material and into the laterally-extending opening in the sealing member to form a doubled thickness of the sleeve having a sealing fold therein to form a seal that is resistant to moisture intrusion into the sleeve.

According to yet another embodiment of the invention, the method includes the step of rolling the bandaging product into a coil and placing the coil in the product storage package with an end of the bandaging product positioned in the sleeve in preparation for dispensing.

According to yet another embodiment of the invention, the method includes the step of inserting the medical material into the sleeve in a coextensive continuum, and rolling the sleeve with the bandaging product therein into a coil and placing the coil in an outer carton.

According to yet another embodiment of the invention, the method includes the step of providing a generally S-shaped clip positioned by a press fit onto an opening edge of the outer carton adjacent an opening in the outer carton through which the medical material is dispensed.

BRIEF DESCRIPTION OF THE DRAWINGS

Some of the objects of the invention have been set forth above. Other objects and advantages of the invention will appear as the description of the invention proceeds when taken in conjunction with the following drawings, in which.

DESCRIPTION OF THE PREFERRED EMBODIMENT

Figure 1:
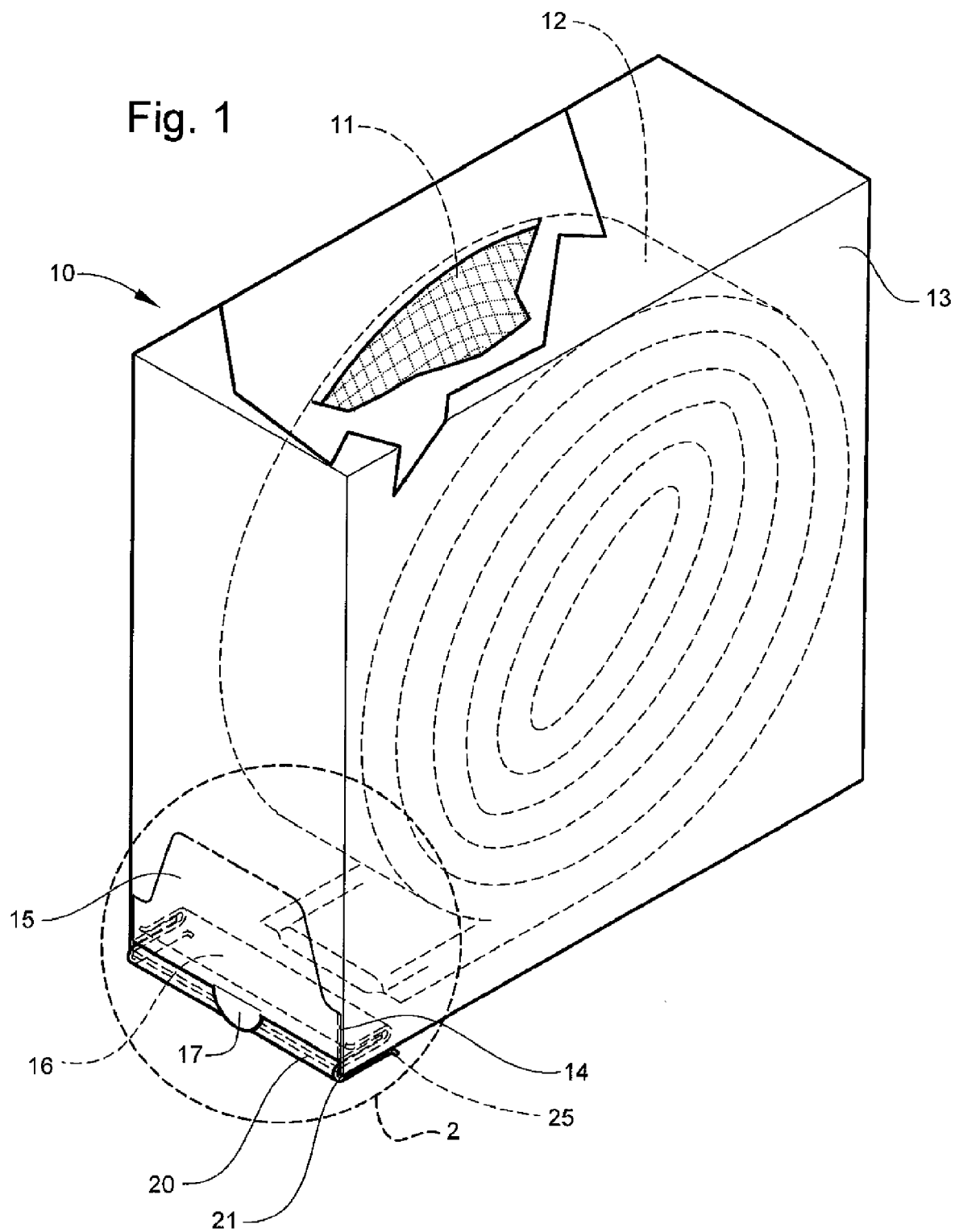
FIG. 1 is an overall perspective view of a medical bandaging product with a resealing means according to an embodiment of the invention.
Figure 2:
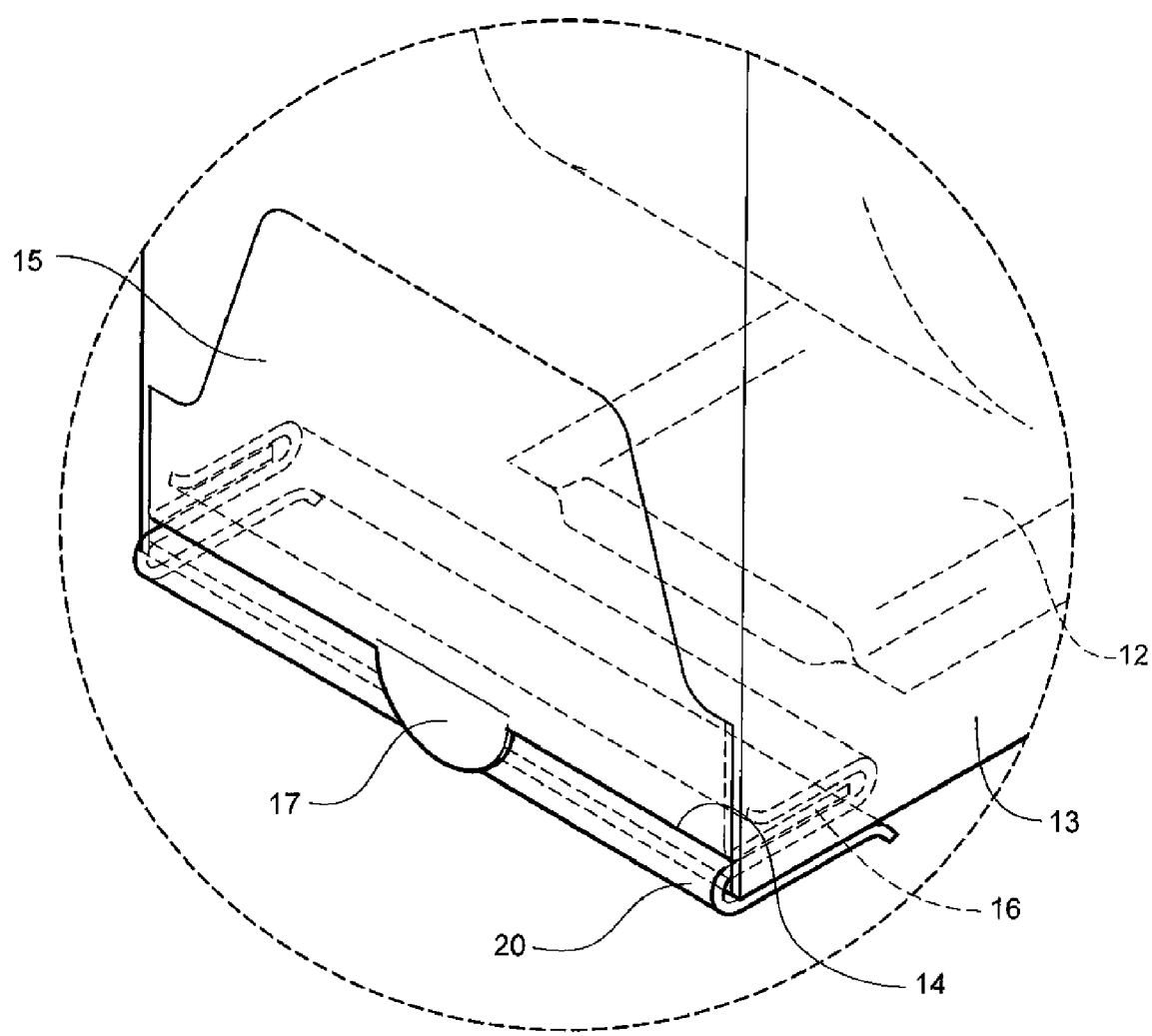
FIG. 2 is an fragmentary enlarged view of the carton closure area of the medical bandaging product.

Referring now specifically to the drawings, a medical bandaging product according to the present invention is shown generally in FIGS. 1 and 2 at 10. The medical bandaging product 10 includes a medical material 11 that may be sold in any convenient length, such as 24 feet, that is positioned in a suitable moisture impervious container, such as a sleeve 12 and is rolled into a coil and positioned in a suitable dispenser, such as a dispenser carton 13. Dispenser carton 13 is provided with a slot 14 at one lower corner through which the medical material 11 and the sleeve 12 extend.

The medical material 11 may be such as disclosed above in U.S. Pat. No. 4,770,299; 4,869,046; 4899,738, 5,003,097, or 6,719,710, or any other roll-form bandage, whether or not moisture-curable, and without regard to the structure of the bandage, whether knitted, woven, or non-woven, or a combination of these constructions.

Figure 3:
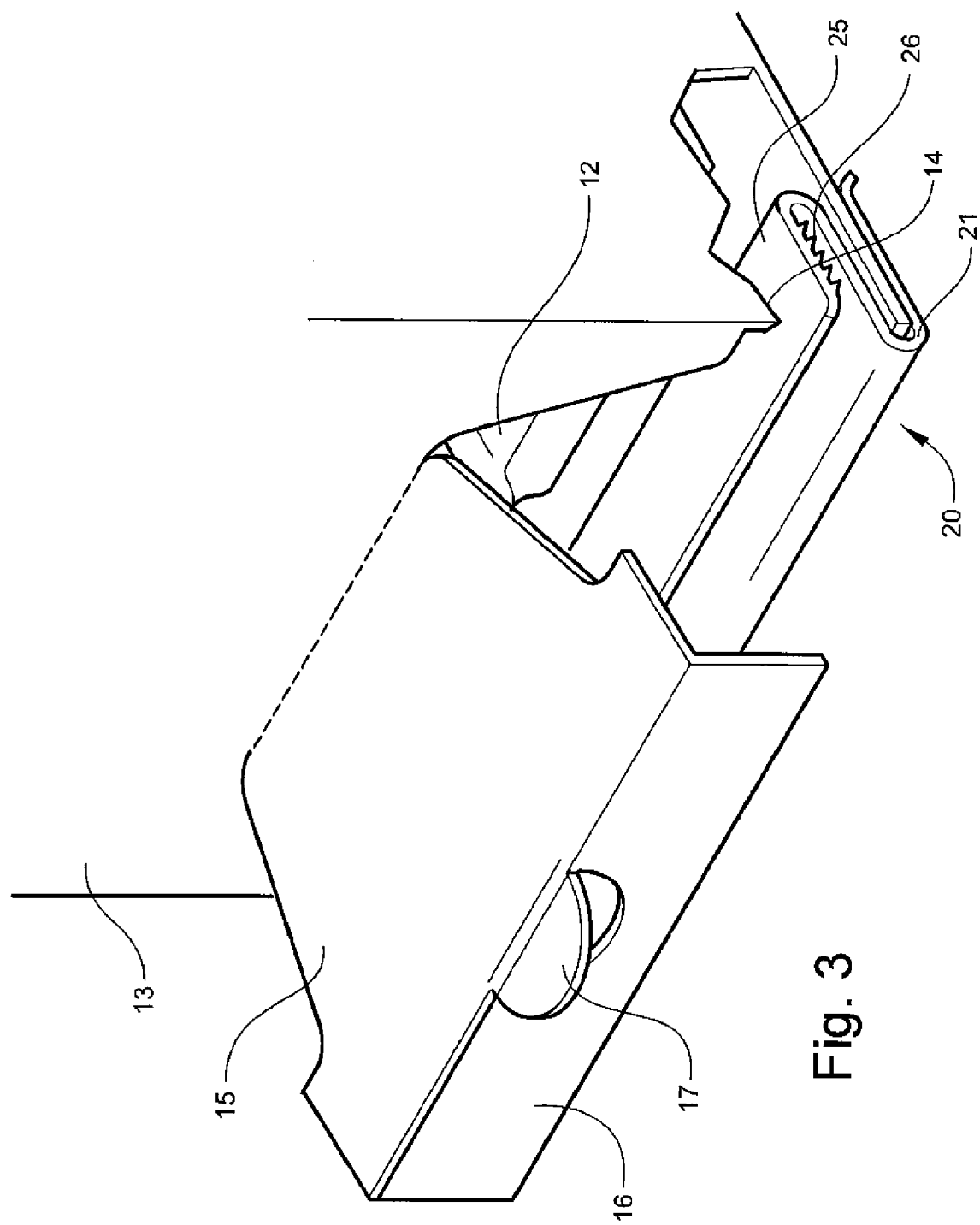
FIG. 3 is an fragmentary enlarged view of the carton closure area of the medical bandaging product, showing the carton flap in an open position.
Figure 4:
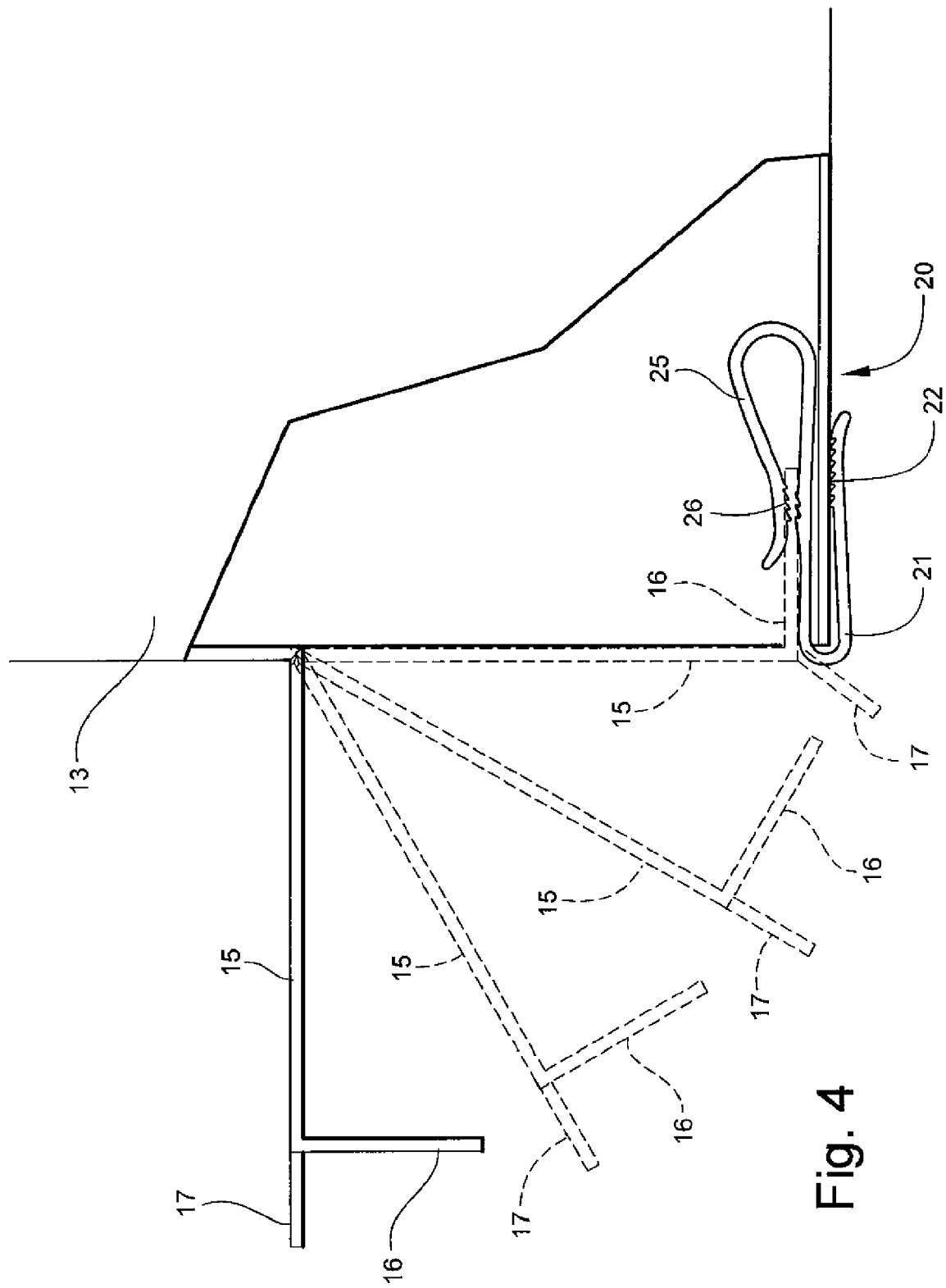
FIG. 4 is a fragmentary enlarged sequential side elevation of the carton closure area showing interaction between the carton flap and carton clip during initial packaging for shipment and storage prior to use.

As is best shown in FIGS. 3 and 4, the carton 13 includes a flap 15 that preferably includes a flap tab 16 and a grip 17 by which the flap 15 can be grasped and pulled away from the carton 13 in order to gain access to the sleeve 12. A clip 20 is positioned on a bottom lip of the carton 13 and defines the bottom of the slot 14. Clip 20 is preferably formed of a lightweight plastic material and has sufficient resilience to allow it to be deformed slightly during application to the carton 13 and during use. Suitable materials include polystyrene, polypropylene, and polyethylene or blends of these and other plastics. The clip 20 may be fabricated by any suitable plastic forming process, such as injection or extrusion-molding, or by cutting or stamping, followed by heating and forming the clip 14 on a mandrel.

Figure 5:
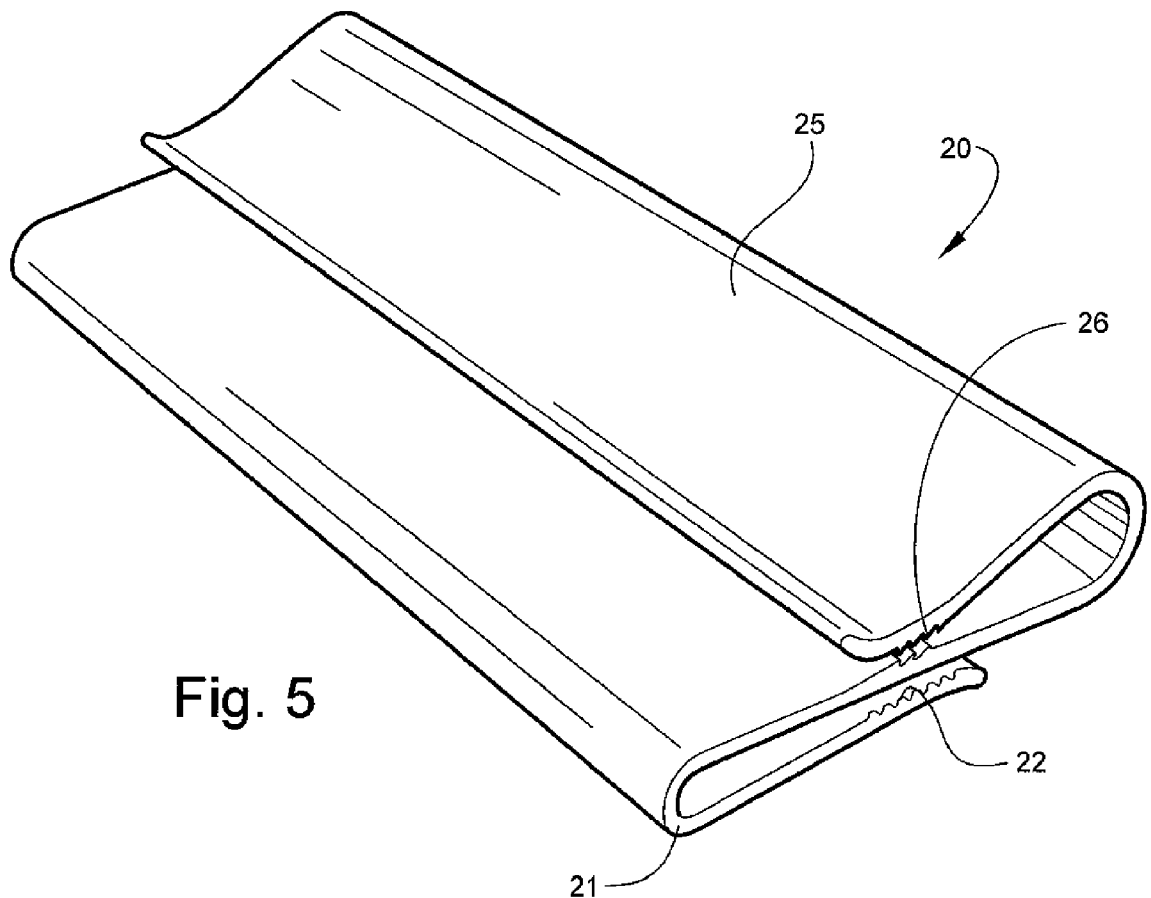
FIG. 5 is a perspective view of a carton clip according to one preferred embodiment of the invention.
Figure 6:
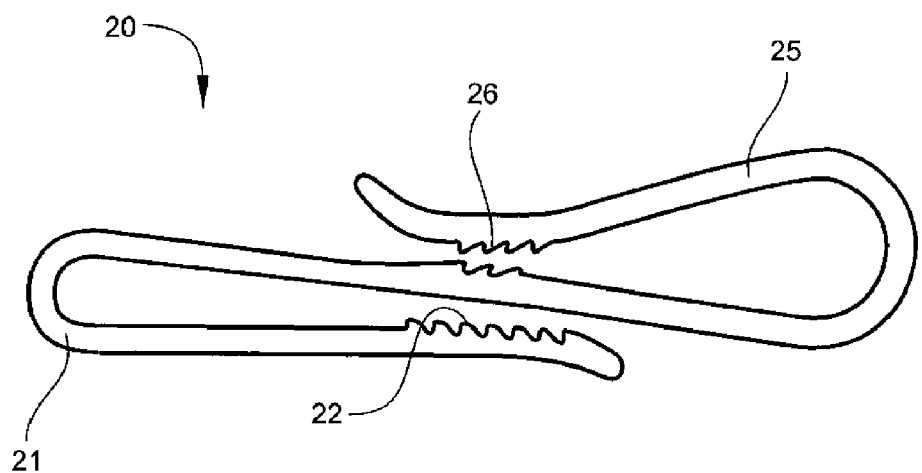
FIG. 6 is an end view of the carton clip according to one preferred embodiment of the invention.

Referring now to FIGS. 5 and 6, the clip 20 has a generally "S"-shaped configuration that includes a doubled-over carton-mounting segment 21. The clip 20 is attached to the carton 13 by inserting the bottom lip of the slot 14 into the carton-mounting segment 21, as shown in FIG. 4. The carton-mounting segment 21 may optionally include teeth 22 to assist in retaining the clip 20 on the carton 13. Other means may be used instead or with the teeth 22, including a light-tack adhesive strip or mechanical attachments.

The clip 20 also includes a doubled-over sealing segment 25 that resides inside the carton 13 behind the slot 14. As best shown in FIG. 4, the flap tab 16 is inserted into the sealing segment 25 of the clip 20 and retains the flap 15 in a closed position. The sealing segment 25 may optionally include teeth 26 to assist in retaining the flap tab 16 in the sealing segment 25 of the clip 20. Other means may be used instead or with the teeth 26, including a light-tack adhesive strip or mechanical attachments.

Note that the end portions of both the carton-mounting segment 21 and the sealing segment 25 are flared open to provide an opening that guides the lip of the carton 13 into the carton-mounting segment 21, and the flap tab 16 into the sealing segment 25, respectively. Also, the volume defined by the sealing segment 25 is larger than the volume of the carton-mounting segment 21 in order to accommodate the material of the sleeve 12, as described below.

Figure 7:
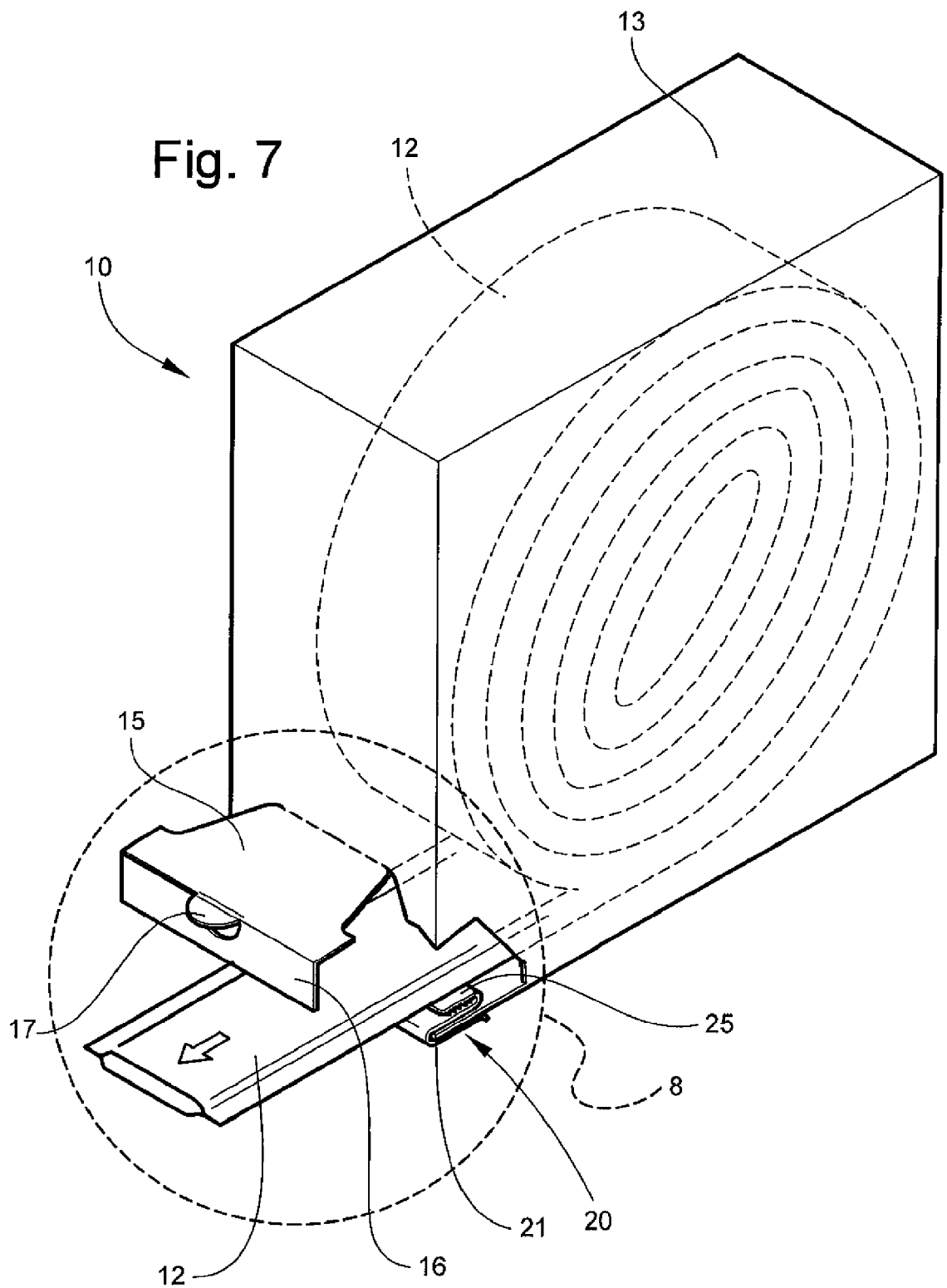
FIG. 7 is a perspective view of a medical bandaging product with a resealing means, showing the manner of dispensing the medical material from the carton.
Figure 8:
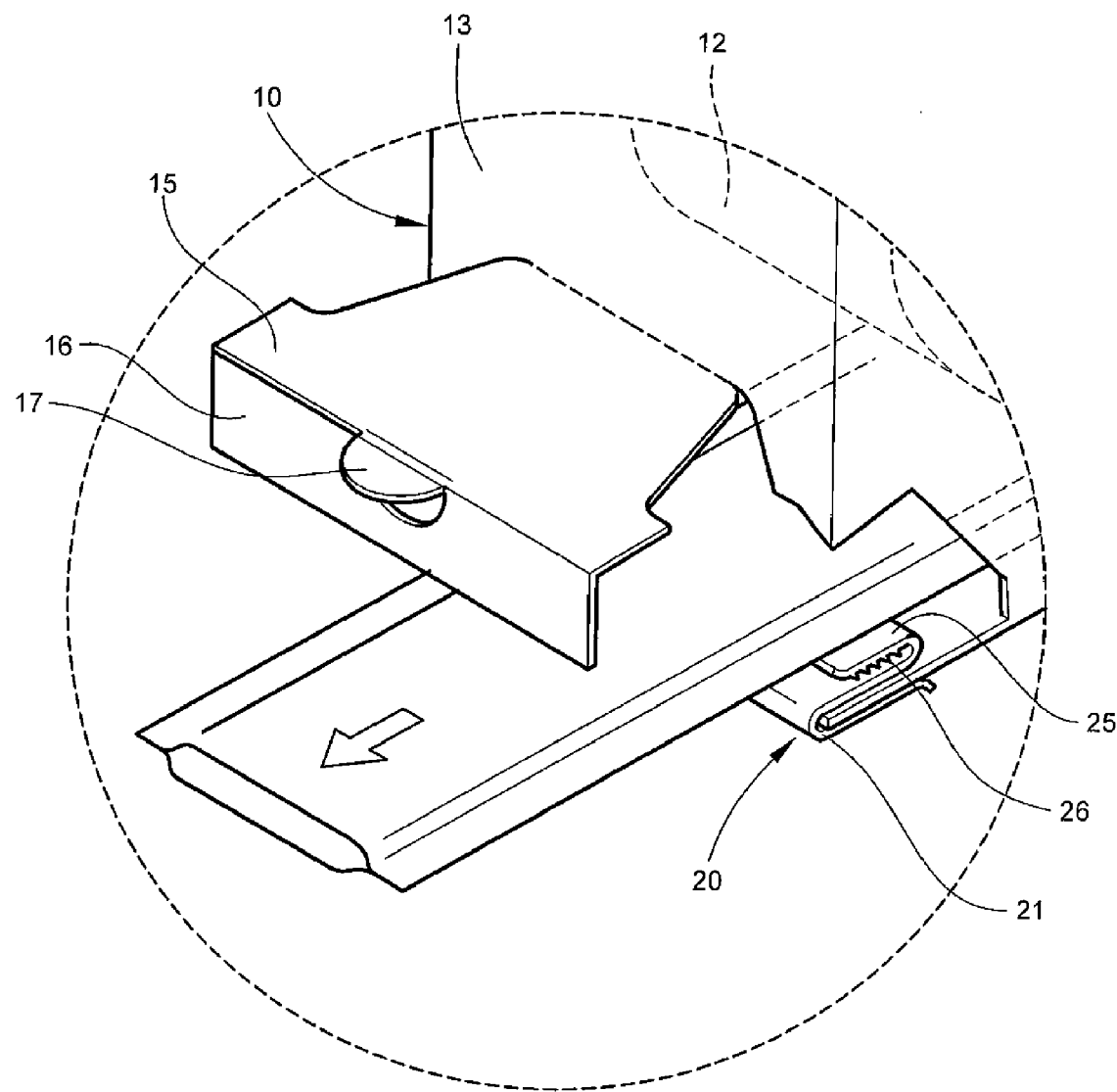
FIG. 8 is a fragmentary enlarged view of the carton closure area of the medical bandaging product showing the medical material being dispensed.
Figure 9:
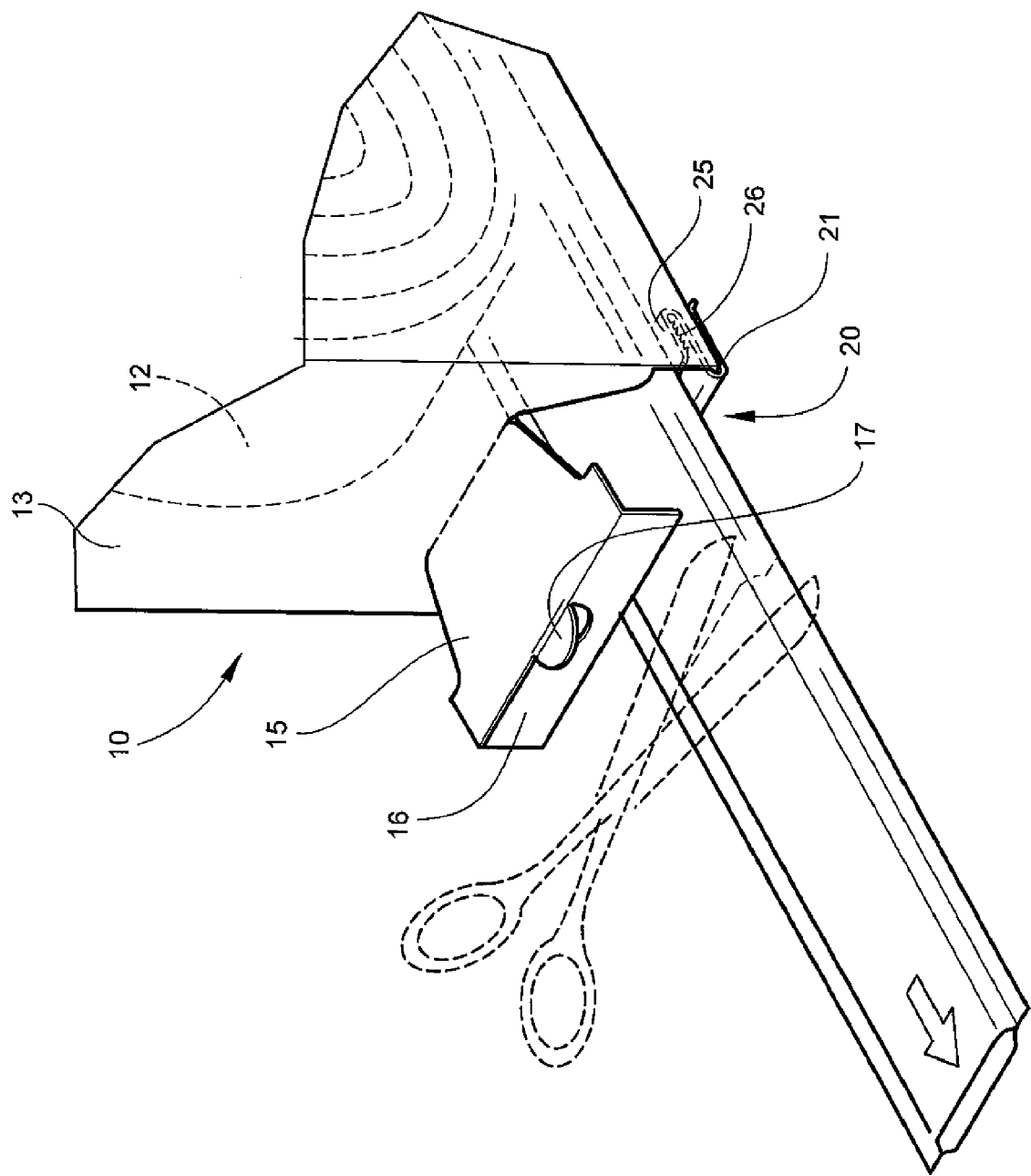
FIG. 9 is a fragmentary enlarged view of the carton closure area of the medical bandaging product showing the medical material being severed from the roll of medical material for use.

Referring now to FIGS. 7-11, use of the clip 20 in dispensing and resealing the sleeve 12 is described. As shown in FIGS. 7 and 8, the carton flap 15 has been opened and the sleeve 12 containing the medical material 11 is withdrawn from the slot 14 in the carton 13. When a medically appropriate length has been withdrawn, the sleeve 12 and medical material 11 in the sleeve 12 are simultaneously cut with scissors or some other cutting implement from the remaining length of medical material 11 and sleeve 12, as is shown in FIG. 9. The cut is made in order to leave a sufficient amount, for example 4-6 inches, of the sleeve 12 extending outwardly from the carton through the slot 14. The medical material 11 is pushed back up into the sleeve 12 remaining within the carton 13 in order that the sleeve 12 outside the carton 13 is empty of medical material 11. The empty length of sleeve 12 is allowed to drape downwardly across the slot 14.

Figure 10:
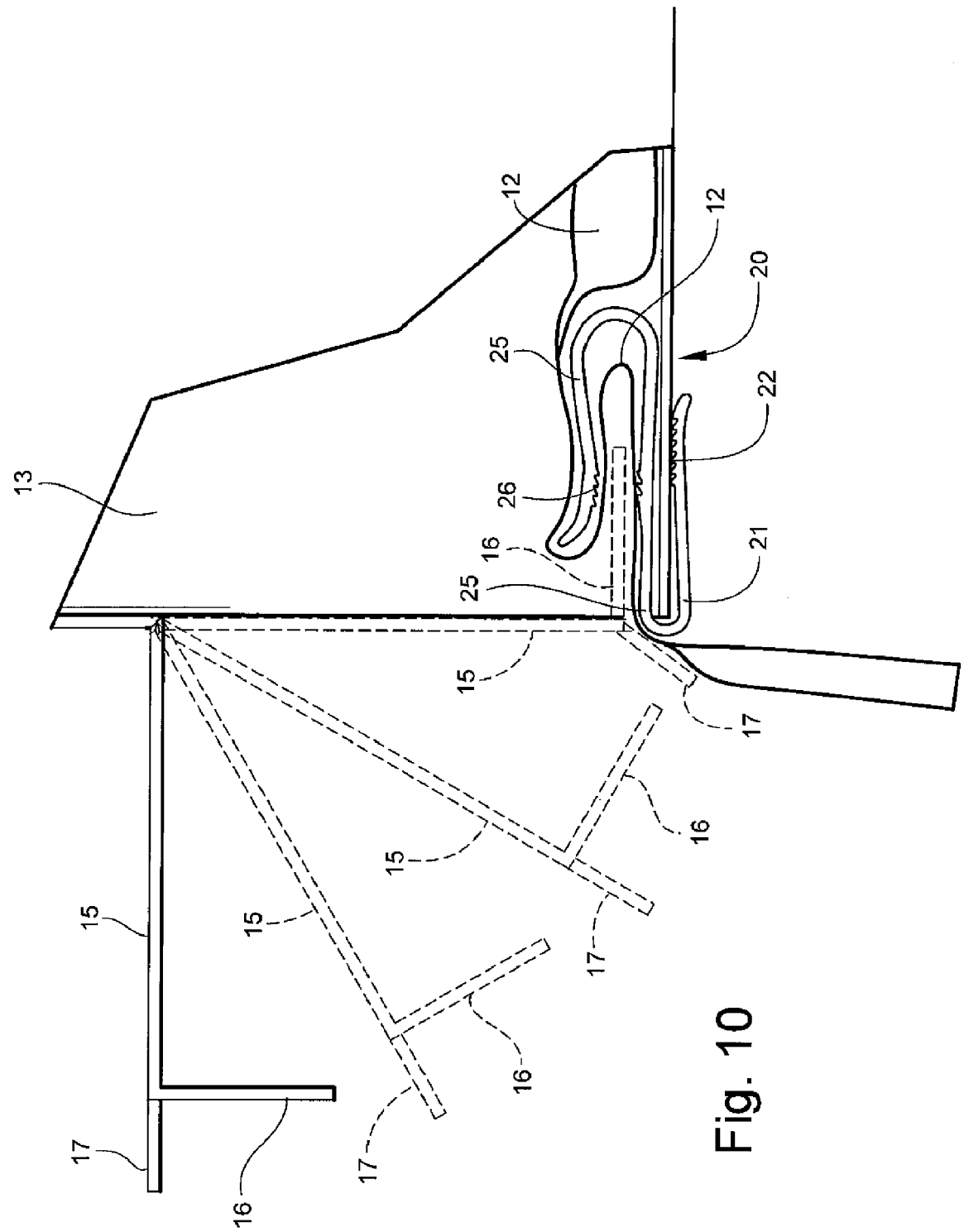
FIG. 10 is a fragmentary enlarged sequential side elevation of the carton closure area showing interaction between the carton flap, carton clip and moisture-impervious package during use.
Figure 11:
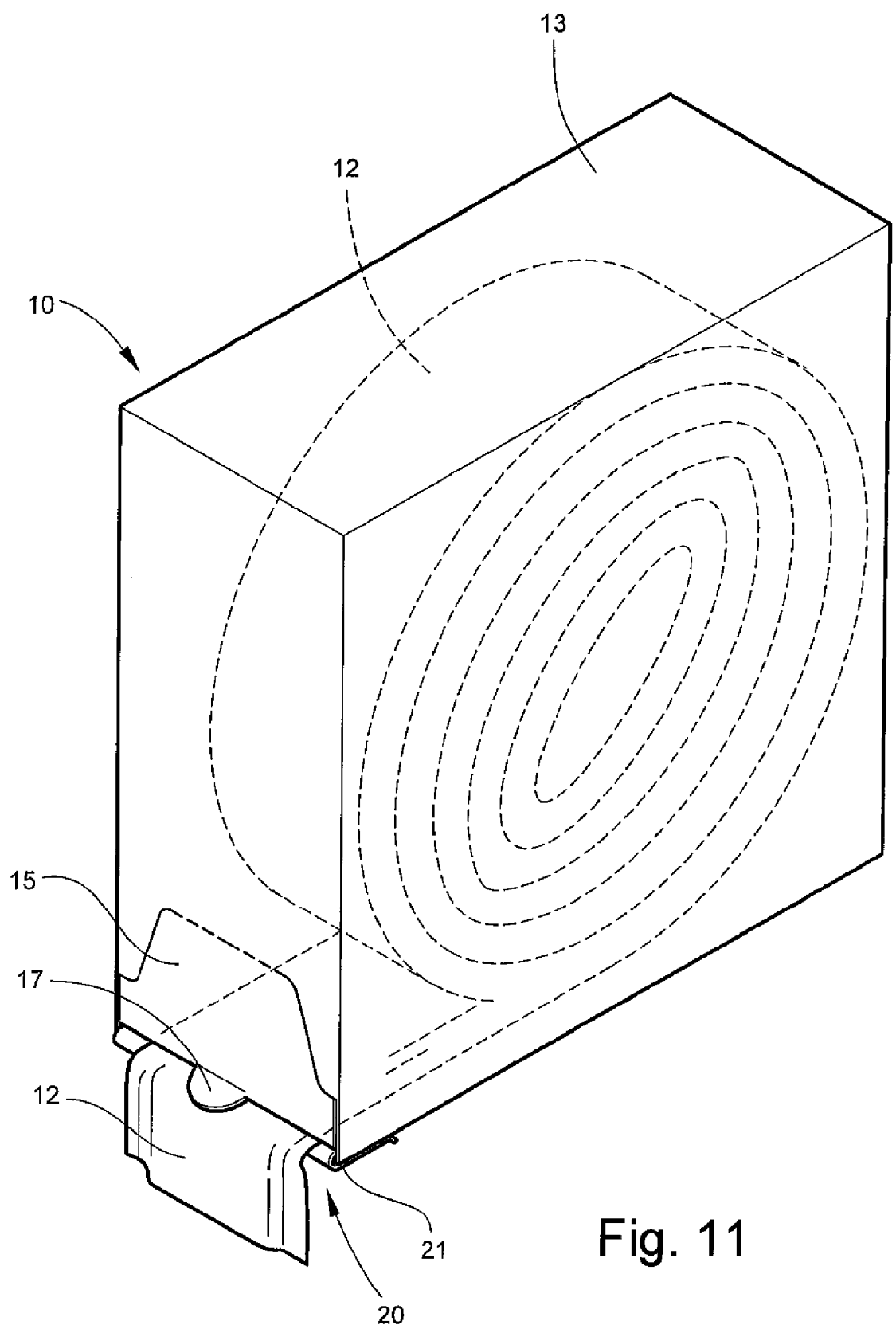
FIG. 11 is a perspective view of the medical bandaging produce showing a length of the moisture-impervious package extending from the carton after removal of the medical material.

As is best shown in FIG. 10, the flap 15 is lowered into closing position, and the flap tab 16 is urged against the empty length of sleeve 12, forcing the empty length of sleeve 12 into the slot 14, and into the sealing segment 25 of the clip 20. As the flap tab 16 is pushed further into the carton 13 through the slot 14, the length of empty sleeve 12 is doubled over on itself, forming a tight bend around the free, innermost end of the flap tab 16. The sealing segment 25 bears against the flap tab 16 and the doubled over thicknesses of the sleeve 12 now residing on the top and bottom surfaces of the flap tab 16, creating a tight seal against penetration of air and moisture, as shown in FIG. 11.

In this sealed position the medical material 11 in the sleeve 12 is maintained in a soft, pliable condition until use. To remove successive lengths of medical material for use, the process described above is repeated.

Depending in the material and construction of the carton 13, it may be desirable to reenforce the flap tab 16 with a stiffener, such as a plastic, metal or reenforced paper sheet suitably adhered to the flap tab 16 in order to prevent or reduce bending or softening of the flap tab 16 during repeated uses.

Figure 12:
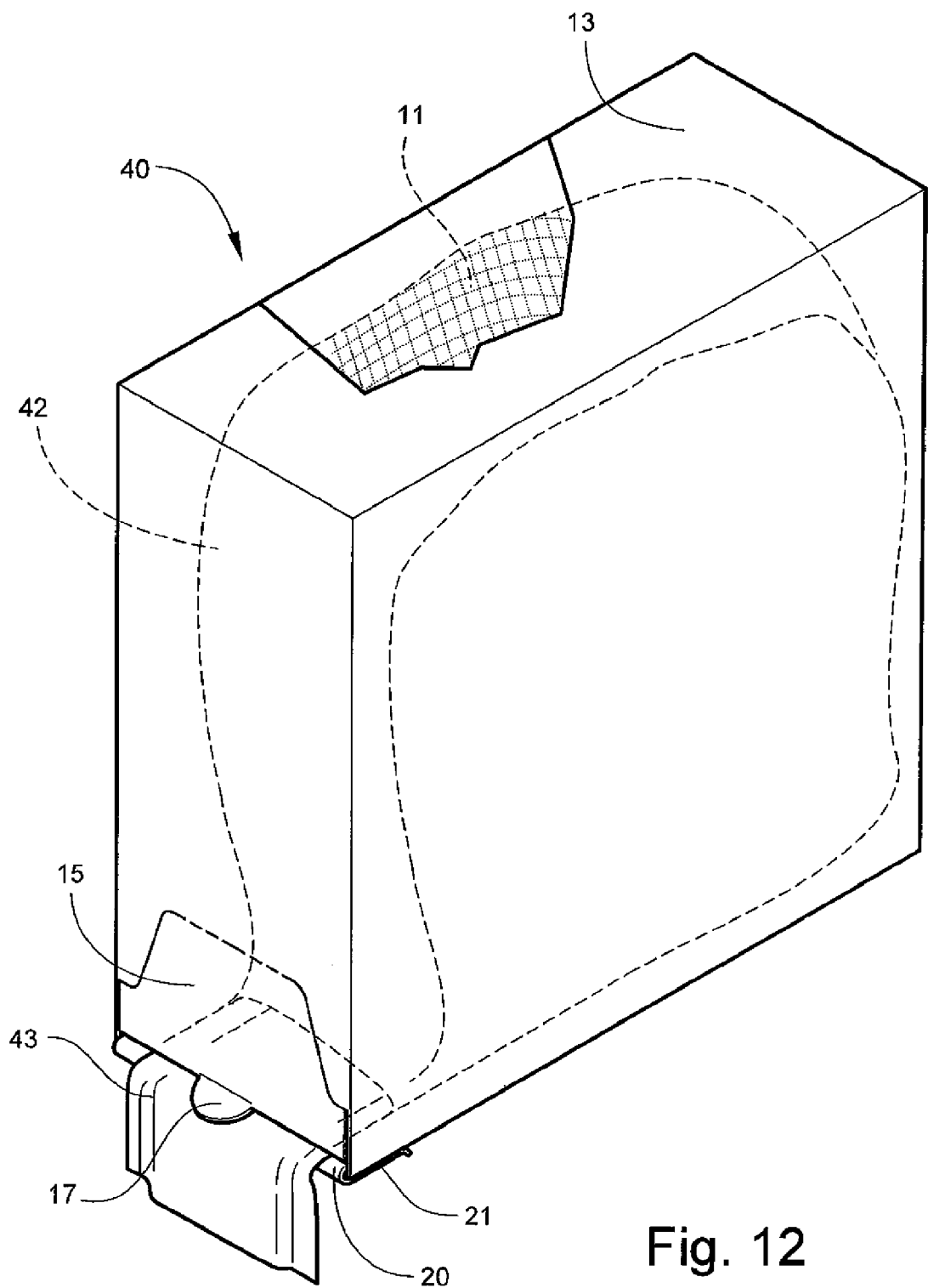
FIG. 12 is an overall perspective view of a medical bandaging produce wherein the medical material is positioned within a moisture-impervious bag for being dispensed through a sleeve extending through an opening in the carton.

Referring now to FIG. 12, an alternative embodiment wherein like reference numerals refer to like elements is shown. In particular, a medical bandaging product 40 includes a medical material 11 that may be sold in any convenient length, such as 24 feet, that is rolled into a coil, and then positioned in a suitable container, such as a moisture impervious bag 12 and positioned in a suitable dispenser, such as a dispenser carton 13. Dispenser carton 13 is provided with a slot 14 at one lower corner through which a sleeve 42 extends. The sleeve 42 is an extension of and communicates with the interior of the bag 43. Thus, instead of feeding successive lengths of both the sleeve 12 and the medical material 11 contained therein through the slot 14, the sleeve 43 remains in its dispensing position outside the carton 13, and when medical material 11 is to be dispensed, the medical material 11 is unrolled and withdrawn through the sleeve 43, where a medically-appropriate length is severed from the roll of material 11 in the bag 43. The sleeve 43 is sealed in the same manner as described above with regard to the sleeve 12.

A medical bandaging product and container is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A method of dispensing and resealing a moisture curable medical material against moisture intrusion, comprising the steps of:
    (a) providing a moisture-impervious product container comprising an elongate sleeve sealable to prevent entry of moisture;
    (b) providing an elongate medical material positioned in the sleeve;
    (c) sealing the medical material in the sleeve against entry of moisture until use, the medical material comprising:
        (i) a substrate;
        (ii) a reactive system impregnated into or coated onto the substrate, the system remaining stable when maintained in substantially moisture-free conditions and hardening upon exposure to sufficient moisture to form a rigid, self supporting structure; and
        (iii) a soft, flexible protective wrapping enclosing the substrate along its length to provide a cushioning barrier between the substrate and the skin of a patient when the material is in use;
    (d) providing a dispensing carton within which the sleeve and medical material positioned therein is contained, the dispensing carton including:
        (i) an opening in the carton through which the medical material is removed through an opening in the container;
        (ii) a sealing member having a laterally-extending opening therein and being carried by the carton adjacent the opening for receiving across the opening in the carton a length of the container devoid of medical material therein, the sealing member having a generally S-shaped body defining a first slot for receiving the tab and doubled thickness of the container, and a second slot for retaining the sealing member on the carton adjacent the opening;
        (iii) a tab for bearing against the length of the container devoid of medical material to form a doubled thickness of the container having a sealing fold therein, wherein the tab is formed on the end of a carton flap that is movable between an open position allowing access through the opening to the container in the carton and a closed position wherein the opening in the carton is covered and the container is maintained in sealing position in the first slot by the tab on the end of the carton flap;
    (e) dispensing a medically appropriate length of medical material; and
    (f) bearing the tab against the length of the sleeve devoid of medical material and into the laterally-extending opening in the sealing member to form a doubled thickness of the sleeve having a sealing fold therein to form a seal that is resistant to moisture intrusion into the sleeve.

2. A method according to claim 1, and including the step of rolling the medical material into a coil and placing the coil in the carton with an end of the medical material positioned in the sleeve in preparation for dispensing.

3. A method according to claim 1, and including the step of inserting the medical material into the sleeve in a coextensive continuum, and rolling the sleeve with the medical material therein into a coil and placing the coil in an outer carton.

4. A method according to claim 3, wherein the sealing member comprises a generally S-shaped clip positioned by a press fit onto an opening edge of the outer carton adjacent an opening in the outer carton through which the medical material is dispensed.

5. A medical bandaging product according to claim 1, wherein the S-shaped body includes first gripping members positioned in the first slot for gripping the sleeve, and second gripping members positioned in the second slot for gripping the carton.

6. A medical bandaging product according to claim 1, wherein the second slot has an enlarged mouth for guiding the tab therein.

7. A method according to claim 1, wherein the container comprises a moisture-impervious sleeve.

* * * * *